(12) United States Patent
Bleicher et al.

(10) Patent No.: US 7,723,538 B2
(45) Date of Patent: May 25, 2010

(54) SULFONAMIDES AS L-CPT1 INHIBITORS

(75) Inventors: Konrad Bleicher, Freiburg (DE); Simona Maria Ceccarelli, Basel (CH); Odile Chomienne, Altkirch (FR); Patrizio Mattei, Riehen (CH); Tanja Schulz-Gasch, Liestal (CH); Christoph Martin Stahl, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 112 days.

(21) Appl. No.: 11/444,765

(22) Filed: Jun. 1, 2006

(65) Prior Publication Data

US 2006/0276494 A1    Dec. 7, 2006

(30) Foreign Application Priority Data

Jun. 6, 2005    (EP) .................................. 05104904

(51) Int. Cl.
C07C 63/04    (2006.01)
(52) U.S. Cl. ..................................................... 562/493
(58) Field of Classification Search ................... 562/493
See application file for complete search history.

(56) References Cited

U.S. PATENT DOCUMENTS 6,528,528 B2 *    3/2003    Connor et al. ............... 514/312
2005/0113450 A1 *    5/2005    Thorarensen et al. ........ 514/562

FOREIGN PATENT DOCUMENTS

WO    WO 2005 115374    * 12/2005

OTHER PUBLICATIONS

ChemBank (http://chembank.broad.harvard.edu/chemistry/viewMolecule.htm?cbid=1917586), printout from website with prior art date disclosed therein.*

Topliss (J. Med. Chem., 1977, v. 20, p. 463-469).*
Hansch et al. ("Substituent Constants for Correlation Analysis in Chemistry and Biology", 1979, Wiley, pp. 48-63 provided of a 339 page book).*
Cannon ("Analog Design" in Burger's Medicinal Chemistry and Drug Discovery, 6th ed. 2003, Wiley, pp. 687-714).*
Jackson et al., 1999, Biochem. J. 341, 483-489.
Jackson et al., 2000, J. Biol. Chem. 275, 19560-19566.
Broadway, N.M. et al, *FEBS Letters*, vol. 371 (1995) p. 137-139 XP-002398463.
Broadway, N.M. et al, *Biochem. Jour.*, vol. 370 (2003) pp. 223-231 XP-002398464.

* cited by examiner

*Primary Examiner*—Rebecca L Anderson
*Assistant Examiner*—Robert Havlin
(74) *Attorney, Agent, or Firm*—George W. Johnston; Dennis P. Tramaloni; Samuel H. Megerditchian

(57) ABSTRACT

The invention is concerned with novel sulfonamide derivatives of formula (I)

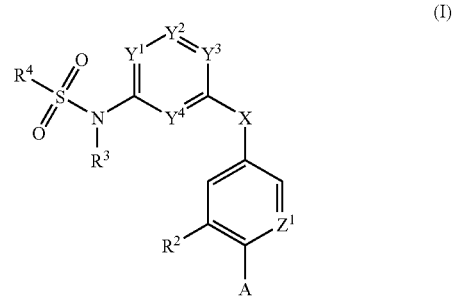

wherein $R^2$, $R^3$, $R^4$, A, X, $Y^1$, $Y^2$, $Y^3$, $Y^4$ and $Z^1$ are as defined in the description and in the claims, as well as physiologically acceptable salts and esters thereof. These compounds inhibit L-CPT1 and can be used as medicaments.

15 Claims, No Drawings

SULFONAMIDES AS L-CPT1 INHIBITORS

PRIORITY TO RELATED APPLICATIONS

This application claims the benefit of European Application No. 05104904.7, filed Jun. 6, 2005, which is hereby incorporated by reference in its entirety.

FIELD OF THE INVENTION

The invention is directed to novel sulfonamide derivatives of the formula (I):

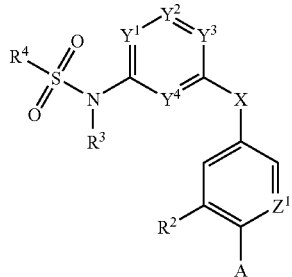

and pharmaceutically acceptable salts and esters thereof.

The invention is also directed to a process for the manufacture of the above compounds, pharmaceutical preparations which contain such compounds as well as the use of these compounds for the production of pharmaceutical preparations.

All documents cited or relied upon below are expressly incorporated herein by reference.

BACKGROUND

High levels of free fatty acids (FFA) lead to an increase of liver mitochondrial β-oxidation, which is crucial to drive efficient gluconeogenesis. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-ter domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates the pyruvate carboxylase and gluconeogenesis. According to the mechanism of action described above, pharmaceutically active substances which inhibit L-CPT1 reduce liver β-oxidation, consequently inhibit gluconeogenesis and therefore counteract hyperglycemia.

SUMMARY OF THE INVENTION

In one embodiment of the present invention, provided is a compound of formula (I):

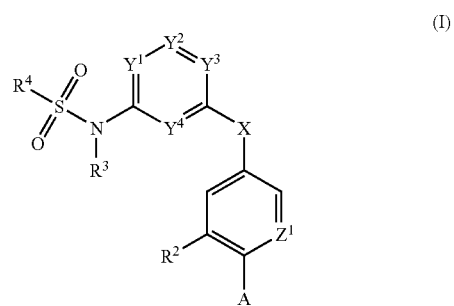

wherein

A is —C(O)OR$^1$ or selected from the group consisting of tetrazol-5-yl, 5-thioxo-4,5-dihydro-[1,2,4]oxadiazol-3-yl, 2-oxo-2,3-dihydro-[1,2,3,5]oxathiadiazol-4-yl and 5-oxo-4,5-dihydro-[1,2,4]oxadiazol-3-yl;

X is —N(R$^5$)C(O)— or —C(O)N(R$^5$)—;

Y$^1$ is N or C(R$^6$);

Y$^2$ is N or C(R$^7$);

Y$^3$ is N or C(H);

Y$^4$ is N or C(R$^8$);

Z$^1$ is N or C(R$^9$);

R$^1$ is hydrogen or lower-alkyl;

R$^2$ is hydrogen, halogen, hydroxy, cyano, lower-alkyl, fluoro-lower-alkyl, lower-alkoxy, fluoro-lower-alkoxy; NH$_2$, N(H, lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ or lower-alkoxy;

R$^3$ is hydrogen, lower-alkyl or lower-alkoxy-lower-alkyl;

R$^4$ is aryl or heteroaryl, which aryl or heteroaryl is optionally substituted with 1 to 3 substituents independently selected from the group consisting of halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$ or N(lower-alkyl)$_2$-S(O)$_2$, NH$_2$—C(O), N(H,lower-alkyl)-C(O), N(lower-alkyl)$_2$-C(O), lower-alkoxy-C(O) or heteroaryl which is optionally substituted with lower-alkyl, halogen, thio-lower-alkoxy, or fluoro-lower-alkyl, wherein lower-alkyl is optionally substituted with hydroxy, NH$_2$, N(H,lower-alkyl) or N(lower-alkyl)$_2$;

R$^5$ is hydrogen, lower-alkyl or lower-alkoxy-lower-alkyl;

R$^6$, R$^7$ and R$^8$ independently from each other are selected from the group consisting of hydrogen, halogen, hydroxy, cyano, lower-alkyl, fluoro-lower-alkyl, lower-alkoxy, fluoro-lower-alkoxy; NH$_2$, N(H,lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ and lower-alkoxy;

R$^9$ is hydrogen, halogen, hydroxy, cyano, lower-alkyl, fluoro-lower-alkyl, lower-alkoxy, fluoro-lower-alkoxy; NH$_2$, N(H, lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ or lower-alkoxy;

and pharmaceutically acceptable salts and esters thereof.

In another embodiment of the present invention, provided is a process for the manufacture of a compound of formula (I), comprising the steps of:

reacting a compound of formula (II)

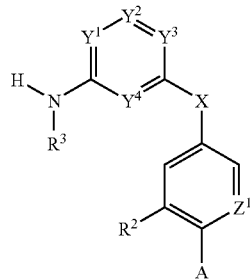

(II)

with a compound LG-S(O)$_2$—R$^4$, wherein R$^2$, R$^3$, R$^4$, A, X, Y$^1$, Y$^2$, Y$^3$, Y$^4$ and Z$^1$ are as defined above and LG is a leaving group, or reacting a compound of formula (III)

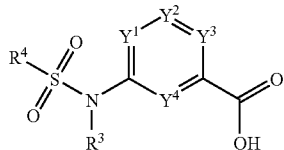

(III)

with a compound of formula (IV)

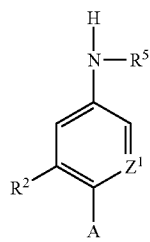

(IV)

wherein R$^2$, R$^3$, R$^4$, R$^5$, A, X, Y$^1$, Y$^2$, Y$^3$, Y$^4$ and Z$^1$ are as defined above, or reacting a compound of formula (V)

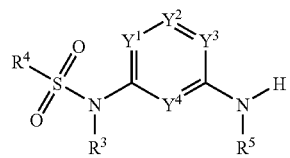

(V)

with a compound of formula (VI)

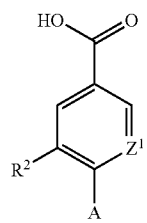

(VI)

wherein R$^2$, R$^3$, R$^4$, R$^5$, A, X, Y$^1$, Y$^2$, Y$^3$, Y$^4$ and Z$^1$ are as defined above.

In a further embodiment of the present invention, provided is a pharmaceutical composition, comprising a therapeutically effective amount of a compound according to formula I, and a pharmaceutically acceptable carrier and/or adjuvant.

In a yet another embodiment of the present invention, provided is a method for the therapeutic and/or prophylactic treatment of diseases which are modulated by L-CPT1 inhibitors, comprising the step of administering a therapeutically effective amount of a compound according to formula I to a human being or animal in need thereof.

DETAILED DESCRIPTION

The present invention relates to novel compounds which inhibit liver carnitine palmitoyl transferase 1 (L-CPT1) activity. The compounds of the present invention can be used as pharmaceutically active agents which are useful in the prevention and/or treatment of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus (also referred to as diabetes type II), obesity, hypertension, insulin resistance syndrome, metabolic syndrome, hyperlipidemia, hypercholesterolemia, fatty liver disease, atherosclerosis, congestive heart failure and renal failure.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups. Alkyl groups can optionally be substituted with hydroxy, halogen, NH$_2$, N(H,lower-alkyl), N(lower-alkyl)$_2$ or lower-alkoxy. Unless specifically mentioned, unsubstituted alkyl groups are preferred.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted with hydroxy, halogen, $NH_2$, N(H,lower-alkyl), N(lower-alkyl)$_2$ or lower-alkoxy. Unless specifically mentioned, unsubstituted lower-alkyl groups are preferred.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidin-1-yl or piperidino etc.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "thio-alkoxy" refers to the group R'—S—, wherein R' is an alkyl. The term "thio-lower-alkoxy" refers to the group R'—S—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl", alone or in combination, relates to the phenyl or naphthyl group, preferably the phenyl group, which can optionally be substituted by 1 to 5, preferably 1 to 3, substituents independently selected from the group consisting of halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, $NH_2$—S(O)$_2$, N(H,lower-alkyl)-S(O)$_2$ or N(lower-alkyl)$_2$-S(O)$_2$, $NH_2$—C(O), N(H,lower-alkyl)-C(O), N(lower-alkyl)$_2$-C(O), lower-alkoxy-C(O) or heteroaryl which is optionally substituted with lower-alkyl, halogen, thio-lower-alkoxy, or fluoro-lower-alkyl, wherein lower-alkyl is optionally substituted with hydroxy, $NH_2$, N(H,lower-alkyl) or N(lower-alkyl)$_2$; Other possible substituents are e.g. hydroxy, amino, carboxy, $NO_2$, dioxo-lower-alkylene (forming e.g. a benzodioxyl group), lower-alkylcarbonyloxy, cycloalkyl and phenyloxy. Preferred substituents are halogen, fluoro-lower-alkyl, lower-alkoxy and fluoro-lower-alkoxy.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl and benzoisoxazolyl. Preferred heteroaryl groups are thiophenyl, isoxazolyl, pyrimidinyl and pyrazolyl. A heteroaryl group may have a substitution pattern as described earlier in connection with the term "aryl". A heteroaryl may preferably be substituted with a heteroaryl that is optionally substituted with 1 to 2 substituents selected from the group consisting of lower-alkyl, fluoro-lower-alkyl and thio-lower-alkyl.

The term "leaving group" refers to a group that may be displaced by a nucleophile (e.g. a secondary amine). Such leaving groups are known in the art and can e.g. be halogen, preferably Cl.

Compounds of formula (I) can form pharmaceutically acceptable salts with bases. Examples of such salts are alkaline, earth-alkaline and ammonium salts such as e.g. Na—, K—, Ca— and trimethylammoniumsalt.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

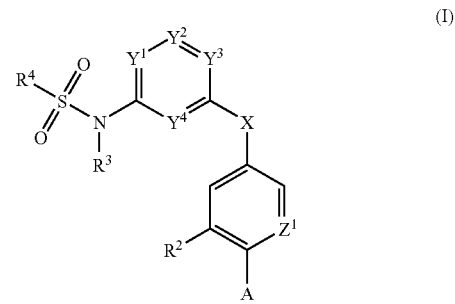

(I)

wherein

A is —$C(O)OR^1$ or selected from the group consisting of tetrazol-5-yl, 5-thioxo-4,5-dihydro-[1,2,4]oxadiazol-3-yl, 2-oxo-2,3-dihydro-[1,2,3,5]oxathiadiazol-4-yl and 5-oxo-4,5-dihydro-[1,2,4]oxadiazol-3-yl;

X is —$N(R^5)C(O)$— or —$C(O)N(R^5)$—;

$Y^1$ is N or $C(R^6)$;

$Y^2$ is N or $C(R^7)$;

$Y^3$ is N or C(H);

$Y^4$ is N or $C(R^8)$;

$Z^1$ is N or $C(R^9)$;

$R^1$ is hydrogen or lower-alkyl;

$R^2$ is hydrogen, halogen, hydroxy, cyano, lower-alkyl, fluoro-lower-alkyl, lower-alkoxy, fluoro-lower-alkoxy; $NH_2$, N(H, lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ or lower-alkoxy;

R$^3$ is hydrogen, lower-alkyl or lower-alkoxy-lower-alkyl;

R$^4$ is aryl or heteroaryl, which aryl or heteroaryl is optionally substituted with 1 to 3 substituents independently selected from the group consisting of halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$ or N(lower-alkyl)$_2$-S(O)$_2$, NH$_2$—C(O), N(H,lower-alkyl)-C(O), N(lower-alkyl)$_2$-C(O), lower-alkoxy-C(O) or heteroaryl which is optionally substituted with lower-alkyl, halogen, thio-lower-alkoxy, or fluoro-lower-alkyl, wherein lower-alkyl is optionally substituted with hydroxy, NH$_2$, N(H,lower-alkyl) or N(lower-alkyl)$_2$;

R$^5$ is hydrogen, lower-alkyl or lower-alkoxy-lower-alkyl;

R$^6$, R$^7$ and R$^8$ independently from each other are selected from the group consisting of hydrogen, halogen, hydroxy, cyano, lower-alkyl, fluoro-lower-alkyl, lower-alkoxy, fluoro-lower-alkoxy; NH$_2$, N(H,lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ and lower-alkoxy;

R$^9$ is hydrogen, halogen, hydroxy, cyano, lower-alkyl, fluoro-lower-alkyl, lower-alkoxy, fluoro-lower-alkoxy; NH$_2$, N(H, lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ or lower-alkoxy;

and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

Preferred compounds of formula (I) are those, wherein A is C(O)OR$^1$ and R$^1$ is as described above. These preferred compounds can be characterised by the following formula (Ib)

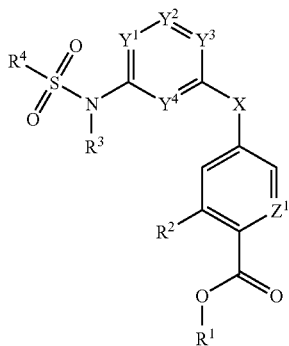

(Ib)

wherein

X is —N(R$^5$)C(O)— or —C(O)N(R$^5$)—;

Y$^1$ is N or C(R$^6$);

Y$^2$ is N or C(R$^7$);

Y$^3$ is N or C(H);

Y$^4$ is N or C(R$^8$);

Z$^1$ is N or C(R$^9$);

R$^1$ is hydrogen or lower-alkyl;

R$^2$ is hydrogen, halogen, hydroxy, cyano, lower-alkyl, fluoro-lower-alkyl, lower-alkoxy, fluoro-lower-alkoxy; NH$_2$, N(H, lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ or lower-alkoxy;

R$^3$ is hydrogen, lower-alkyl or lower-alkoxy-lower-alkyl;

R$^4$ is aryl or heteroaryl, which aryl or heteroaryl is optionally substituted with 1 to 3 substituents independently selected from the group consisting of halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$ or N(lower-alkyl)$_2$-S(O)$_2$, NH$_2$—C(O), N(H,lower-alkyl)-C(O), N(lower-alkyl)$_2$-C(O), lower-alkoxy-C(O) or heteroaryl which is optionally substituted with lower-alkyl, halogen, thio-lower-alkoxy, or fluoro-lower-alkyl, wherein lower-alkyl is optionally substituted with hydroxy, NH$_2$, N(H,lower-alkyl) or N(lower-alkyl)$_2$;

R$^5$ is hydrogen, lower-alkyl or lower-alkoxy-lower-alkyl;

R$^6$, R$^7$ and R$^8$ independently from each other are selected from the group consisting of hydrogen, halogen, hydroxy, cyano, lower-alkyl, fluoro-lower-alkyl, lower-alkoxy, fluoro-lower-alkoxy; NH$_2$, N(H,lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ and lower-alkoxy;

R$^9$ is hydrogen, halogen, hydroxy, cyano, lower-alkyl, fluoro-lower-alkyl, lower-alkoxy, fluoro-lower-alkoxy; NH$_2$, N(H, lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ or lower-alkoxy;

and pharmaceutically acceptable salts and esters thereof.

When reference to compounds of formula (I) is made in this text, this includes a reference to formula (Ia) and (Ib).

Preferred compounds of formula (I) as described above are those, wherein R$^1$ is hydrogen. Other preferred compounds are those, wherein R$^2$ is hydrogen, halogen or lower-alkoxy, more preferably wherein R$^2$ is hydrogen. Other preferred compounds of formula (I) as described above are those, wherein R$^3$ is hydrogen.

A further preferred embodiment of the present invention refers to compounds of formula (I) as described above, wherein R$^4$ is phenyl which is optionally substituted with 1 to 3 substituents independently selected from the group consisting of halogen, fluoro-lower-alkyl, lower-alkoxy and fluoro-lower-alkoxy, or R$^4$ is thiophenyl which is substituted with a heteroaryl selected from the group consisting of isoxazolyl, pyrimidinyl and pyrazolyl, which heteroaryl is optionally substituted with 1 to 2 substituents selected from the group consisting of lower-alkyl, fluoro-lower-alkyl and thio-lower-alkoxy, or R$^4$ is naphthalinyl. Compounds as described above, wherein R$^4$ is phenyl which is substituted with 1 to 2 substituents independently selected from the group consisting of halogen and lower-alkoxy are more preferred. Even more preferably, R⁴ is 3-chloro-phenyl, 3,4-dichloro-phenyl, 3,5-dichloro-phenyl or 5-chloro-2-methoxy-phenyl.

Another preferred embodiment of the present invention is related to compounds of formula (I) as described above, wherein X is —C(O)N(R⁵)— and R⁵ is as defined above. Such compounds are characterised by formula (Ia)

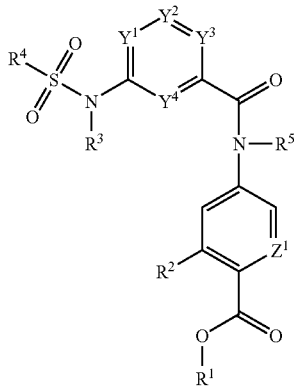

In such compounds, R⁵ preferably is hydrogen.

Other preferred compounds of formula (I) of the present invention are those, wherein Y¹ is C(R⁶) and R⁶ is as defined above. Preferably, R⁶ is hydrogen, halogen or lower-alkoxy, more preferably R⁶ is hydrogen, chlorine or methoxy. Other preferred compounds of the present invention are those, wherein Y² is C(R⁷) and R⁷ is as defined above. Preferably, R⁷ is hydrogen or lower alkoxy, more preferably R⁷ is hydrogen or methoxy.

Furthermore, those compounds of formula (I) as described above are preferred, wherein Y³ is C(H). Other preferred compounds of formula (I) are those, wherein Y⁴ is C(R⁸) and R⁸ is as defined above, particularly those wherein R⁸ is hydrogen. Compounds of formula (I) as described above, wherein Z¹ is N or C(R⁹) and R⁹ is hydrogen, halogen or lower-alkoxy, are also preferred, especially those, wherein Z¹ is C(R⁹) and R⁹ is hydrogen.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:
4-(3-Benzenesulfonylamino-benzoylamino)-benzoic acid,
4-[3-(4-Methoxy-benzenesulfonylamino)-benzoylamino]-benzoic acid,
4-[3-(3-Fluoro-benzenesulfonylamino)-benzoylamino]-benzoic acid,
4-[3-(Naphthalene-2-sulfonylamino)-benzoylamino]-benzoic acid,
4-[3-(3,4-Dichloro-benzenesulfonylamino)-benzoylamino]-benzoic acid,
4-[3-(2-Methoxy-benzenesulfonylamino)-benzoylamino]-benzoic acid,
4-[3-(3-Methoxy-benzenesulfonylamino)-benzoylamino]-benzoic acid,
4-[3-(2-Fluoro-benzenesulfonylamino)-benzoylamino]-benzoic acid,
4-[3-(3-Chloro-benzenesulfonylamino)-benzoylamino]-benzoic acid,
4-[3-(3-Trifluoromethyl-benzenesulfonylamino)-benzoylamino]-benzoic acid,
4-[3-(3,5-Dichloro-benzenesulfonylamino)-benzoylamino]-benzoic acid,
4-[3-(5-Chloro-2-methoxy-benzenesulfonylamino)-benzoylamino]-benzoic acid,
4-[3-(3-Difluoromethoxy-benzenesulfonylamino)-benzoylamino]-benzoic acid,
4-[3-(5-Isoxazol-3-yl-thiophene-2-sulfonylamino)-benzoylamino]-benzoic acid,
4-{3-[5-(2-Methylsulfanyl-pyrimidin-4-yl)-thiophene-2-sulfonylamino]-benzoylamino}-benzoic acid,
4-{3-[5-(2-Methyl-5-trifluoromethyl-2H-pyrazol-3-yl)-thiophene-2-sulfonylamino]-benzoylamino}-benzoic acid,
2-Methoxy-4-[3-(3-trifluoromethyl-benzenesulfonylamino)-benzoylamino]-benzoic acid,
4-[3-(3,5-Dichloro-benzenesulfonylamino)-benzoylamino]-2-methoxy-benzoic acid,
4-[3-(3,4-Dichloro-benzenesulfonylamino)-benzoylamino]-2-methoxy-benzoic acid,
4-[3-(3-Chloro-benzenesulfonylamino)-benzoylamino]-2-methoxy-benzoic acid,
4-[4-Chloro-3-(3-chloro-benzenesulfonylamino)-benzoylamino]-benzoic acid,
4-[4-Chloro-3-(3,5-dichloro-benzenesulfonylamino)-benzoylamino]-benzoic acid,
4-[4-Chloro-3-(3-trifluoromethyl-benzenesulfonylamino)-benzoylamino]-benzoic acid,
4-[4-Chloro-3-(3-trifluoromethoxy-benzenesulfonylamino)-benzoylamino]-benzoic acid,
4-[4-Chloro-3-(5-chloro-2-methoxy-benzenesulfonylamino)-benzoylamino]-benzoic acid,
4-[4-Chloro-3-(3,4-dichloro-benzenesulfonylamino)-benzoylamino]-benzoic acid,
4-[4-Chloro-3-(benzenesulfonylamino)-benzoylamino]-benzoic acid,
4-[4-Chloro-3-(2,5-dichloro-benzenesulfonylamino)-benzoylamino]-benzoic acid,
4-[4-Chloro-3-(3-fluoro-benzenesulfonylamino)-benzoylamino]-benzoic acid,
4-[4-Chloro-3-(2,5-dimethoxy-benzenesulfonylamino)-benzoylamino]-benzoic acid,
4-[3-(3-Chloro-benzenesulfonylamino)-4,5-dimethoxy-benzoylamino]-benzoic acid,
4-[3-(3,5-Dichloro-benzenesulfonylamino)-4,5-dimethoxy-benzoylamino]-benzoic acid,
4-[3,4-Dimethoxy-5-(3-trifluoromethyl-benzenesulfonylamino)-benzoylamino]-benzoic acid,
4-[3-(5-Chloro-2-methoxy-benzenesulfonylamino)-4,5-dimethoxy-benzoylamino]-benzoic acid,
4-[3-(3,4-Dichloro-benzenesulfonylamino)-4,5-dimethoxy-benzoylamino]-benzoic acid,
4-[3-(benzenesulfonylamino)-4,5-dimethoxy-benzoylamino]-benzoic acid,
4-[3-(2,5-Dichloro-benzenesulfonylamino)-4,5-dimethoxy-benzoylamino]-benzoic acid,
4-[3-(3-Chloro-benzenesulfonylamino)-benzoylamino]-2-fluoro-benzoic acid, and
5-[3-(3-Chloro-benzenesulfonylamino)-benzoylamino]-pyridine-2-carboxylic acid, and pharmaceutically acceptable salts and esters thereof.

Particularly preferred compounds of formula (I) are those selected from the group consisting of:
4-[3-(3,4-Dichloro-benzenesulfonylamino)-benzoylamino]-benzoic acid,
4-[3-(3-Chloro-benzenesulfonylamino)-benzoylamino]-benzoic acid,
4-[3-(3,5-Dichloro-benzenesulfonylamino)-benzoylamino]-benzoic acid,
4-[3-(5-Chloro-2-methoxy-benzenesulfonylamino)-benzoylamino]-benzoic acid, 4-[4-Chloro-3-(3-chloro-benzenesulfonylamino)-benzoylamino]-benzoic acid,
4-[4-Chloro-3-(3,5-dichloro-benzenesulfonylamino)-benzoylamino]-benzoic acid,
4-[4-Chloro-3-(5-chloro-2-methoxy-benzenesulfonylamino)-benzoylamino]-benzoic acid,
4-[3-(3,5-Dichloro-benzenesulfonylamino)-4,5-dimethoxy-benzoylamino]-benzoic acid, and
4-[3-(5-Chloro-2-methoxy-benzenesulfonylamino)-4,5-dimethoxy-benzoylamino]-benzoic acid, and pharmaceutically acceptable salts and esters thereof.

Other preferred compounds of formula (I) are those selected from the group consisting of:
3-(3-Chloro-benzenesulfonylamino)-[4-(tetrazol-5-yl)-phenyl]-benzamide,
3-(5-Chloro-2-methoxy-benzenesulfonylamino)-[4-(tetrazol-5-yl)-phenyl]-benzamide,
3-(5-Chloro-2-methoxy-benzenesulfonylamino)-N-[4-(5-thioxo-4,5-dihydro-[1,2,4]oxadiazol-3-yl)-phenyl]-benzamide,
3-(5-Chloro-2-methoxy-benzenesulfonylamino)-N-[4-(2-oxo-2,3-dihydro-[1,2,3,5]oxathiadiazol-4-yl)-phenyl]-benzamide,
3-(5-Chloro-2-methoxy-benzenesulfonylamino)-N-[4-(5-oxo-4,5-dihydro-[1,2,4]oxadiazol-3-yl)-phenyl]-benzamide, and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (II)

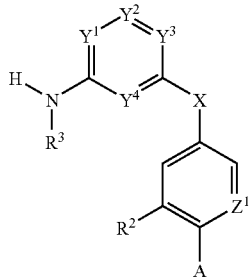

(II)

with a compound LG-S(O)$_2$—R$^4$, wherein R$^2$, R$^3$, R$^4$, A, X, Y$^1$, Y$^2$, Y$^3$, Y$^4$ and Z$^1$ are as defined above and LG is a leaving group (such as e.g. halogen, preferably Cl), or reacting a compound of formula (III)

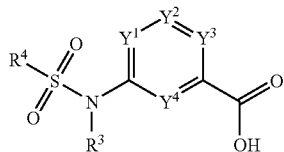

(III)

with a compound of formula (IV)

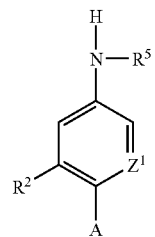

(IV)

wherein R$^2$, R$^3$, R$^4$, R$^5$, A, X, Y$^1$, Y$^2$, Y$^3$, Y$^4$ and Z$^1$ are as defined above, or reacting a compound of formula (V)

(V)

with a compound of formula (VI)

(VI)

wherein R$^2$, R$^3$, R$^4$, R$^5$, A, X, Y$^1$, Y$^2$, Y$^3$, Y$^4$ and Z$^1$ are as defined above.

The reaction of a compound of formula (II) with a compound LG-S(O)$_2$—R$^4$ can be carried out under conditions well known to the person skilled in the art. Such reactions of a compound of formula (II) can conveniently be carried out for example by mixing a compound of formula (II) with a compound LG-S(O)$_2$—R$^4$ in dichloromethane at room temperature in the presence of a base, as for example pyridine. Alternative, reactions of a compound of formula (II) can be carried out by heating the latter with a compound LG-S(O)$_2$—R$^4$ in toluene at the reflux temperature, optionally in the presence of a base, as for example triethylamine. Appropriate leaving group can for example be chlorine.

The reaction of a compound of formula (III) with a compound of formula (IV) can be carried out under conditions well known to the person skilled in the art. Such reactions of a compound of formula (II) can conveniently be carried out for example by mixing a compound of formula (III) with a compound of formula (IV) in dimethylformamide in the presence of a base, like for example diisopropylethylamine, and a condensing agent. Appropriate condensing agents can be for example O-(7-benzotriazol-1-yl)-N,N,N',N'-tetramethyluronium-tetrafluoroborat (TBTU), O-(7-azabenzotriazol-1-yl)-N,N,N',N'-tetramethyluronium-hexaflurophophat (HATU) or others well known to the person skilled in the art.

The reaction of a compound of formula (V) with a compound of formula (VI) can be carried out under conditions well known to the person skilled in the art. Such reactions of a compound of formula (II) can conveniently be carried out for example by mixing a compound of formula (V) with a compound of formula (VI) in dimethylformamide in the presence of a base, like for example diisopropylethylamine, and a condensing agent. Appropriate condensing agents can be for example TBTU, HATU or others well known to the person skilled in the art.

The present invention also relates to compounds of formula (I) as defined above, when prepared by a process as described above.

The compounds of formula (I), (II), (III), (IV), (V) and (VI) can be prepared by methods known in the art or as described below. Unless otherwise indicated, the substituents $R^1$, $R^2$, $R^3$, $R^4$, $R^5$, X, m and n are as described above.

The following schemes 1, 2 and 3 illustrate the methods of preparation of the compounds of the present invention. Unless otherwise specified, all starting products and intermediates are commercially available or can be prepared by methods known in the art or by analogous methods.

Scheme 1:

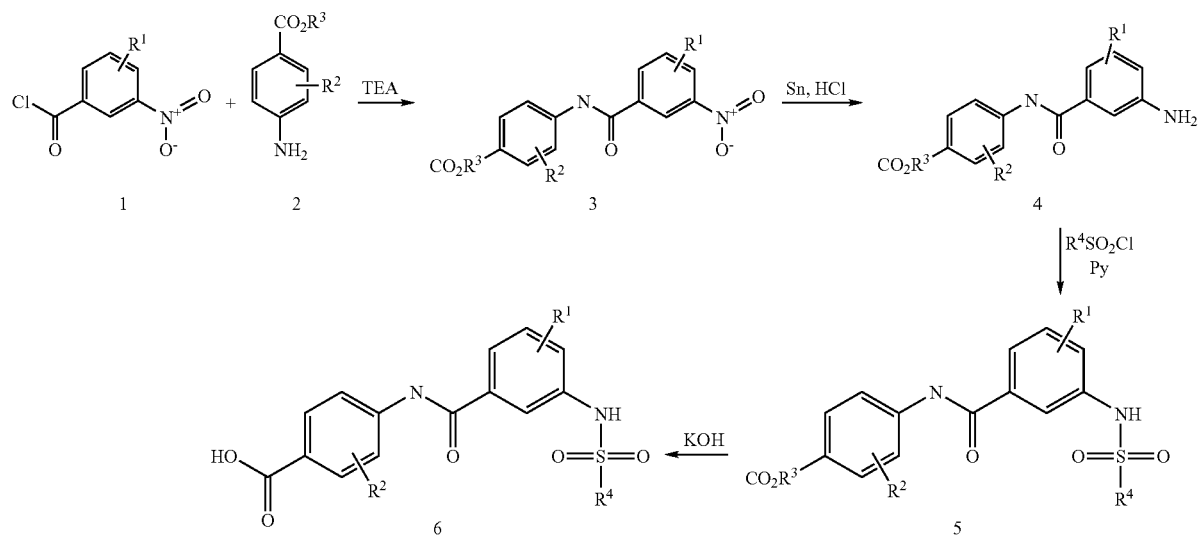

Compounds of general formula 6 can be prepared by hydrolysis of the corresponding esters 5. These are accessed by the reaction of a generic 4-(3-amino-benzoylamino)-benzoic acid ethyl ester 4 with a sulfonyl chloride, according to known methods. 4-(3-Amino-benzoylamino)-benzoic acid ethyl esters 4 can be generated by reduction of the corresponding nitro compounds 3, which are generated by the reaction of the 3-nitro-benzoyl chlorides 1 with a generic 4-amino-benzoic acid ethyl ester 2.

Scheme 2:

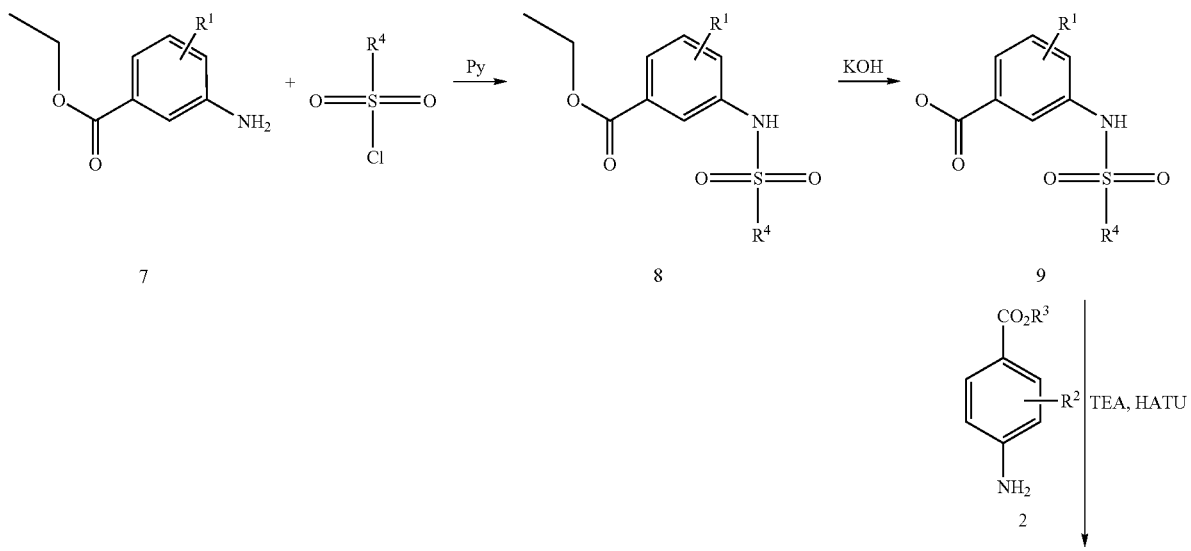

-continued

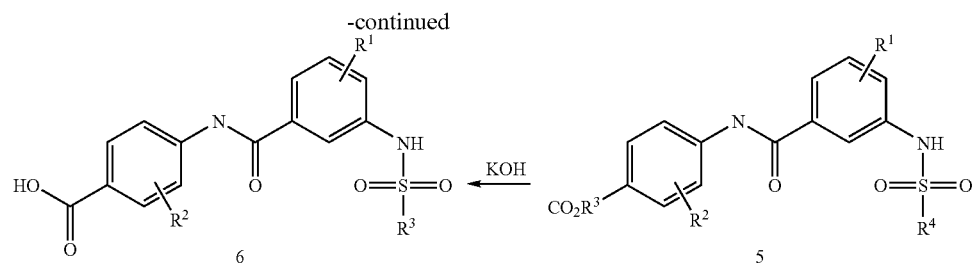

Alternatively, esters of general formula 5 can be generated by reaction of 3-benzenesulfonylamino-benzoic acids 9 with a generic 4-amino-benzoic acid ethyl ester 2,3-Benzenesulfonylamino-benzoic acids 9 are accessed by hydrolysis of the corresponding esters 8, produced by reaction of 3-aminobenzoic acid ethyl esters 7 with a sulfonyl chloride in the presence of pyridine.

Compounds of general formula 12, wherein A is selected from the group consisting of 1H-tetrazol-2-yl, 4H-[1,2,4]oxadiazol-3-yl-5-one, 4H-[1,2,4]oxadiazol-3-yl-5-thione or 3H-[1,2,3,5]oxathiadiazol-4-yl-2-oxide, can be prepared starting from compounds of general formula 10, which can be prepared in analogy to the schemes 1 and 2 above. Compounds of general formula 10 can be reacted with an azide Scheme 3:

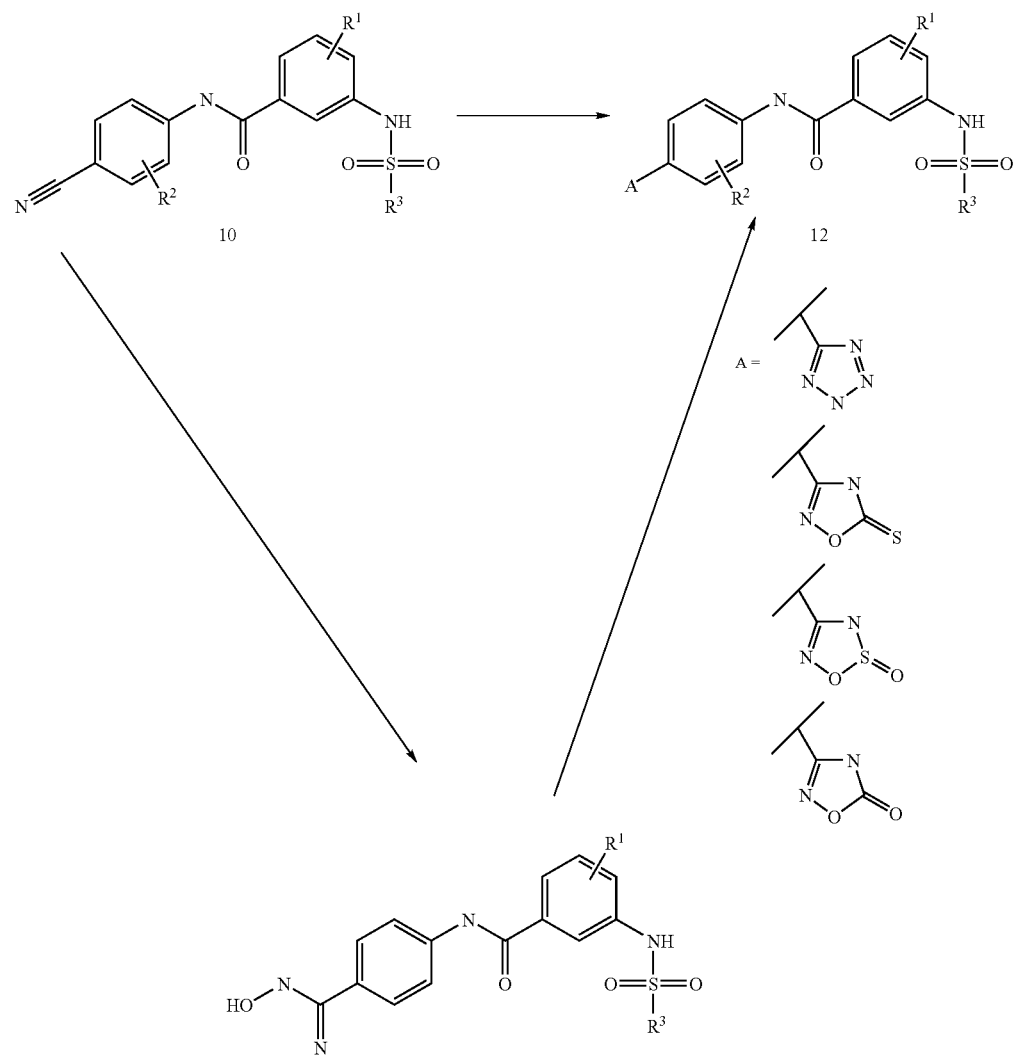

source, like for example ammonium azide or tin azide, at temperatures between 20° C. and 200° C. to generate compounds of formula 12 where A is 1H-tetrazol-2-yl. Compounds of general formula 10 can be converted by reaction with hydroxylamine to the corresponding hydroxyamidines of general formula 11, which can then be reacted with chloroformic acid derivatives to generate compounds of general formula 12 where A is -[1,2,4]oxadiazol-3-yl-5-one. Reaction of compounds of general formula 11 with 1,1'-thiocarbonyldiimidazole under basic conditions generates compounds of general formula 12 where A is 4H-[1,2,4]oxadiazol-3-yl-5-thione. Alternative, reaction of compounds of general formula 11 with thionyl chloride generates compounds of general formula 12 where A is 3H-[1,2,3,5]oxathiadiazol-4-yl-2-oxide.

Compounds of formula (I) can form salts with physiologically compatible bases. Examples of such salts are alkaline, earth-alkaline and ammonium salts such as e.g. Na—, K—, Ca— and trimethylammoniumsalt. One method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofurane-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU). Pharmaceutically acceptable esters can furthermore be prepared by treatment of a suitable hydroxy group present in the molecule with a suitable acid, optionally or if necessary in the presence of a condensating agent as described above.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit liver carnitine palmitoyl transferase 1 (L-CPT1) activity. The compounds of the present invention can therefore be used in the treatment and/or prophylaxis of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by L-CPT1 inhibitors, particularly as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound as defined above to a human being or animal.

The invention also embraces the use of compounds as defined above for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention also relates to the use of compounds as described above for the preparation of medicaments for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound as described above.

Prevention and/or treatment of hyperglycemia and non insulin dependent diabetes mellitus is the preferred indication.

The following tests were carried out in order to determine the activity of the compounds of the present invention. Background information on the performed assays can be found in: Jackson et al., 1999, Biochem. J. 341, 483-489 and Jackson et al., 2000, J. Biol. Chem. 275, 19560-19566.

Human liver and muscle CPT1 cDNAs and rat CPT2 cDNA were subcloned in pGAPZB or pGAPZA, respectively. These plasmids were used to transform *P. pastoris* strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH 7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB) also called Ellman's reagent. The HS-CoA released on the formation of acylcarnitine from carnitine (500 μM) and palmitoyl-CoA (80 μM) reduced DTNB (300 μM) forming 5-mercapto-(2-nitrobenzoic acid) witch absorbed at 410 nm with a molar coefficient extinction of 13600 $M^{-1} \cdot cm^{-1}$. The assay buffer contained 120 mM KCl, 25 mM Tris, pH 7.4, 1 mM EDTA. This assay was used for the identification of selective inhibitors of the liver CPT1 isoform versus the muscle CPT1 and CPT2 isoforms.

The compounds according to formula (I) preferably have an IC50 value below 10 µM, preferably 10 nM to 10 µM, more preferably 10 nM to 5 µM. The following table shows data for some examples.

| Example | L-CPT1 inhibition IC$_{50}$ [µmol/l] |
|---|---|
| 5 | 0.1922 |
| 21 | 0.1526 |
| 32 | 0.8805 |

A method of screening for a compound which modulates CPT1 activity is also provided, compromising providing cell-free extracts from cells expressing CPT1, contacting said compound with CPT1 in said extract, and measuring the release of HS-CoA by CPT1 in the presence of carnitine, palmitoyl-CoA and a reagent which produces a detectable signal in the presence of thiols.

Such a reagent can either be a reagent which produces fluorescence in the presence of thiols. Such a reagent can be selected from the group consisting of monobromobimane (mBrB), ammonium 7-flourobenzo-2-oxa-1,3-diazole-4-sulfonate (SBD-F), ammonium 7-fluorobenzo-2-oxa-1,3-diazole-4-sulfonamide (ABD-F), fluorescein isothiocyanate, bromomethylfluorescein, 4-aminosulfonyl-7-fluoro-2,1,3-benzoxadiazole (ABD-F), fluorescein-5-maleimide, and 6-iodoacetamidofluorescein. Such a reagent can also be a reagent which produces a chromophore in the presence of thiols. Such a reagent can be selected from the group consisting of 4,4'-dipyrdyl disulfide (4-PDS), 2,2'-dipyrdyl disulfide (2-DPS), 2-chloro-1-methylpyridinium iodide (CMPI), 2-chloro-1-methylquinolinium tetrafluoroborate (CQMT), DTNB, 5-(2-aminoethyl)dithio-2-nitrobenzoate (ADNB), 2,2' or 4,4'-dithiodipyridine (DTDP).

Preferably, said reagent is DTNB which can be quantitated by measuring the formation of 5-mercapto-(2-nitrobenzoic acid) which absorbs at 410 nm.

Preferably, said CPT1 is mammalian, more preferably rat, sheep or human, most preferably liver muscle or brain.

In a preferred embodiment, said cells expressing CPT1 are yeast cells, more preferably *P. pastoris* or *S. cerevisiae* cells.

Preferably, said quantitation of 5-mercapto-(2-nitrobenzoic acid) is performed with a spectrophotometer.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner.

EXAMPLES

Example 1

4-(3-Benzenesulfonylamino-benzoylamino)-benzoic acid 4-(3-Benzenesulfonylamino-benzoylamino)-benzoic acid was prepared as illustrated in scheme 1:

Step A)

A solution of 4-amino benzoic acid ethyl ester (1.95 g, 11.8 mmol) in dry dichloromethane (20.0 ml) was treated with triethylamine (1.31 g, 13.0 mmol) and cooled to 0° C. 3-Nitrobenzoyl chloride (2.00 g, 10.8 mmol) was added portion wise over 5 min. The mixture was stirred at 0° C. for 5 min, then at room temperature for 10 min. The reaction was quenched by addition of 20 ml of saturated NaHCO$_3$. The organic phase was separated and filtered washing with dichloromethane. Drying of the solid under high vacuum yielded 4-(3-nitro-benzoylamino)-benzoic acid ethyl ester as a white solid (2.52 g, 74%), MS (ISP): m/e=315.1 (M+H$^+$).

Step B)

A solution of 4-(3-nitro-benzoylamino)-benzoic acid ethyl ester (0.50 g, 1.59 mmol) in THF (5.0 ml) was treated with tin metal (0.38 g, 3.18 mmol) and 6N HCl (2.5 ml). The mixture was warmed to 50° C. and stirred for 30 min. After cooling to room temperature, the solvent was evaporated, and the residue treated with 10% aqueous NaOH (10.0 ml). The resulting suspension was filtered, washing with water. The solid was dissolved in THF and treated with $Na_2SO_4$. After filtration, the filtrate was evaporated to yield 4-(3-amino-benzoylamino)-benzoic acid ethyl ester (0.36 g, 80%) as a light yellow solid, MS (ISP): m/e=285.3 ($M+H^+$).

Step C)

A solution of 4-(3-amino-benzoylamino)-benzoic acid ethyl ester (50.0 mg, 0.18 mmol) in pyridine (0.40 ml) was treated with a solution of benzensulfonyl chloride (31.0 mg, 0.18 mmol) in pyridine (0.10 ml). The mixture was stirred at room temperature overnight. The solvent was evaporated, yielding crude 4-(3-benzenesulfonylamino-benzoylamino)-benzoic acid ethyl ester, MS (ISP): m/e=425.1 ($M+H^+$), which was used as such in the next step.

Step D)

A solution of crude 4-(3-benzenesulfonylamino-benzoylamino)-benzoic acid ethyl ester (75.0 mg, 0.18 mmol) in methanol (0.30 ml) was treated with a 2.55 M solution of KOH in water (0.21 ml). The mixture was stirred at 55° C. for 40 min, then acidified with 2N HCl (0.40 ml) to pH~1. The mixture was diluted with 1-methyl pyrrolidinone (2.00 ml) and purified by preparative HPLC (ZORBAX Eclipse XDB-C18, 21.2×50 mm, 5 μm, gradient acetonitrile/water+0.1% formic acid). The title compound (14.4 mg, 21%) was obtained as an off-white solid, MS (ISP): m/e=394.9 (M−H).

Example 2

4-[3-(4-Methoxy-benzenesulfonylamino)-benzoylamino]-benzoic acid ethyl ester

4-[3-(4-Methoxy-benzenesulfonylamino)-benzoylamino]-benzoic acid ethyl ester, MS (ISP): m/e=425.1 (M−H), was prepared in analogy to example 1, steps A to D. Step C was performed using 4-methoxy-benzensulfonyl chloride and yielded 4-[3-(4-methoxy-benzenesulfonylamino)-benzoylamino]-benzoic acid ethyl ester, which was hydrolyzed in step D.

Example 3

4-[3-(3-Fluoro-benzenesulfonylamino)-benzoylamino]-benzoic acid

4-[3-(3-Fluoro-benzenesulfonylamino)-benzoylamino]-benzoic acid, MS (ISP): m/e=413.1 (M−H), was prepared in analogy to example 1, steps A to D. Step C was performed using 3-fluoro-benzensulfonyl chloride and yielded 4-[3-(3-fluoro-benzenesulfonylamino)-benzoylamino]-benzoic acid ethyl ester, which was hydrolyzed in step D.

Example 4

4-[3-(Naphthalene-2-sulfonylamino)-benzoylamino]-benzoic acid

4-[3-(Naphthalene-2-sulfonylamino)-benzoylamino]-benzoic acid, MS (ISP): m/e=445.1 (M−H), was prepared in analogy to example 1, steps A to D. Step C was performed using naphthalene-2-sulfonyl chloride and yielded 4-[3-(naphthalene-2-sulfonylamino)-benzoylamino]-benzoic acid ethyl ester, which was hydrolyzed in step D.

Example 5

4-[3-(3,4-Dichloro-benzenesulfonylamino)-benzoylamino]-benzoic acid

4-[3-(3,4-Dichloro-benzenesulfonylamino)-benzoylamino]-benzoic acid, MS (ISP): m/e=462.9 (M−H), was prepared in analogy to example 1, steps A to D. Step C was performed using 3,4-dichloro-benzenesulfonyl chloride and yielded 4-[3-(3,4-dichloro-benzenesulfonylamino)-benzoylamino]-benzoic acid ethyl ester, which was hydrolyzed in step D.

Example 6

4-[3-(2-Methoxy-benzenesulfonylamino)-benzoylamino]-benzoic acid

4-[3-(2-Methoxy-benzenesulfonylamino)-benzoylamino]-benzoic acid, MS (ISP): m/e=425.1 (M−H), was prepared in analogy to example 1, steps A to D. Step C was performed using 2-methoxy-benzenesulfonyl chloride and yielded 4-[3-(2-methoxy-benzenesulfonylamino)-benzoylamino]-benzoic acid ethyl ester, which was hydrolyzed in step D.

Example 7

4-[3-(3-Methoxy-benzenesulfonylamino)-benzoylamino]-benzoic acid

4-[3-(3-Methoxy-benzenesulfonylamino)-benzoylamino]-benzoic acid, MS (ISP): m/e=425.1 (M−H), was prepared in analogy to example 1, steps A to D. Step C was performed using 3-methoxy-benzenesulfonyl chloride and yielded 4-[3-(3-methoxy-benzenesulfonylamino)-benzoylamino]-benzoic acid ethyl ester, which was hydrolyzed in step D.

Example 8

4-[3-(2-Fluoro-benzenesulfonylamino)-benzoylamino]-benzoic acid

4-[3-(2-Fluoro-benzenesulfonylamino)-benzoylamino]-benzoic acid, MS (ISP): m/e=413.1 (M−H), was prepared in analogy to example 1, steps A to D. Step C was performed using 2-fluoro-benzensulfonyl chloride and yielded 4-[3-(2-fluoro-benzenesulfonylamino)-benzoylamino]-benzoic acid ethyl ester, which was hydrolyzed in step D.

Example 9

4-[3-(3-Chloro-benzenesulfonylamino)-benzoylamino]-benzoic acid

4-[3-(3-Chloro-benzenesulfonylamino)-benzoylamino]-benzoic acid, MS (ISP): m/e=429.2 (M−H), was prepared in analogy to example 1, steps A to D. Step C was performed using 3-chloro-benzensulfonyl chloride and yielded 4-[3-(3-chloro-benzenesulfonylamino)-benzoylamino]-benzoic acid ethyl ester, which was hydrolyzed in step D.

Example 10

4-[3-(3-Trifluoromethyl-benzenesulfonylamino)-benzoylamino]-benzoic acid

4-[3-(3-Trifluoromethyl-benzenesulfonylamino)-benzoylamino]-benzoic acid, MS (ISP): m/e=463.3 (M–H), was prepared in analogy to example 1, steps A to D. Step C was performed using 3-trifluoromethyl-benzenesulfonyl chloride and yielded 4-[3-(3-trifluoromethyl-benzenesulfonylamino)-benzoylamino]-benzoic acid ethyl ester, which was hydrolyzed in step D.

Example 11

4-[3-(3,5-Dichloro-benzenesulfonylamino)-benzoylamino]-benzoic acid

4-[3-(3,5-Dichloro-benzenesulfonylamino)-benzoylamino]-benzoic acid, MS (ISP): m/e=463.2 (M–H), was prepared in analogy to example 1, steps A to D. Step C was performed using 3,5-dichloro-benzenesulfonyl chloride and yielded 4-[3-(3,5-dichloro-benzenesulfonylamino)-benzoylamino]-benzoic acid ethyl ester, which was hydrolyzed in step D.

Example 12

4-[3-(5-Chloro-2-methoxy-benzenesulfonylamino)-benzoylamino]-benzoic acid

4-[3-(5-Chloro-2-methoxy-benzenesulfonylamino)-benzoylamino]-benzoic acid, MS (ISP): m/e=459.0 (M–H), was prepared in analogy to example 1, steps A to D. Step C was performed using 5-chloro-2-methoxy-benzenesulfonyl chloride and yielded 4-[3-(5-chloro-2-methoxy-benzenesulfonylamino)-benzoylamino]-benzoic acid ethyl ester, which was hydrolyzed in step D.

Example 13

4-[3-(3-Difluoromethoxy-benzenesulfonylamino)-benzoylamino]-benzoic acid

4-[3-(3-Difluoromethoxy-benzenesulfonylamino)-benzoylamino]-benzoic acid, MS (ISP): m/e=461.1 (M–H), was prepared in analogy to example 1, steps A to D. Step C was performed using 5-chloro-2-methoxy-benzenesulfonyl chloride and yielded 4-[3-(5-chloro-2-methoxy-benzenesulfonylamino)-benzoylamino]-benzoic acid ethyl ester, which was hydrolyzed in step D.

Example 14

4-[3-(5-Isoxazol-3-yl-thiophene-2-sulfonylamino)-benzoylamino]-benzoic acid

4-[3-(5-Isoxazol-3-yl-thiophene-2-sulfonylamino)-benzoylamino]-benzoic acid, MS (ISP): m/e=468.1 (M–H), was prepared in analogy to example 1, steps A to D. Step C was performed using 5-isoxazol-3-yl-thiophene-2-sulfonyl chloride and yielded 4-[3-(5-isoxazol-3-yl-thiophene-2-sulfonylamino)-benzoylamino]-benzoic acid ethyl ester, which was hydrolyzed in step D.

Example 15

4-{3-[5-(2-Methylsulfanyl-pyrimidin-4-yl)-thiophene-2-sulfonylamino]-benzoylamino}-benzoic acid 4-{3-[5-(2-Methylsulfanyl-pyrimidin-4-yl)-thiophene-2-sulfonylamino]-benzoylamino}-benzoic acid, MS (ISP): m/e=525.2 (M–H), was prepared in analogy to example 1, steps A to D. Step C was performed using 5-(2-methylsulfanyl-pyrimidin-4-yl)-thiophene-2-sulfonyl chloride and yielded 4-{3-[5-(2-methylsulfanyl-pyrimidin-4-yl)-thiophene-2-sulfonylamino]-benzoylamino}-benzoic acid ethyl ester, which was hydrolyzed in step D.

Example 16

4-{3-[5-(2-Methyl-5-trifluoromethyl-2H-pyrazol-3-yl)-thiophene-2-sulfonylamino]-benzoylamino}-benzoic acid 4-{3-[5-(2-Methyl-5-trifluoromethyl-2H-pyrazol-3-yl)-thiophene-2-sulfonlyamino]-benzoylamino}-benzoic acid, MS (ISP): m/e=549.2 (M–H), was prepared in analogy to example 1, steps A to D. Step C was performed using 5-(2-methyl-5-trifluoromethyl-2H-pyrazol-3-yl)-thiophene-2-sulfonyl chloride and yielded 4-{3-[5-(2-methyl-5-trifluoromethyl-2H-pyrazol-3-yl)-thiophene-2-sulfonylamino]-benzoylamino}-benzoic acid ethyl ester, which was hydrolyzed in step D.

Example 17

2-Methoxy-4-[3-(3-trifluoromethyl-benzenesulfonylamino)-benzoylamino]-benzoic acid 2-Methoxy-4-[3-(3-trifluoromethyl-benzenesulfonylamino)-benzoylamino]-benzoic acid, MS (ISP): m/e=493.3 (M–H), was prepared in analogy to example 1, steps A to D. Step A was performed using 4-amino-2-methoxy-benzoic acid ethyl ester and yielded 2-methoxy-4-(3-nitro-benzoylamino)-benzoic acid ethyl ester. This was reduced to 4-(3-amino-benzoylamino)-2-methoxy-benzoic acid ethyl ester in step B. This was coupled with 3-trifluoromethyl-benzenesulfonyl chloride in step C, yielding 2-methoxy-4-[3-(3-trifluoromethyl-benzenesulfonylamino)-benzoylamino]-benzoic acid ethyl ester, which was hydrolyzed in step D.

Example 18

4-[3-(3,5-Dichloro-benzenesulfonylamino)-benzoylamino]-2-methoxy-benzoic acid

4-[3-(3,5-Dichloro-benzenesulfonylamino)-benzoylamino]-2-methoxy-benzoic acid, MS (ISP): m/e=493.2 (M–H), was prepared in analogy to example 17, steps A to D. Step C was performed using 3,5-dichloro-benzenesulfonyl chloride and yielded 4-[3-(3,5-dichloro-benzenesulfonylamino)-benzoylamino]-2-methoxy-benzoic acid ethyl ester, which was hydrolyzed in step D.

Example 19

4-[3-(3,4-Dichloro-benzenesulfonylamino)-benzoylamino]-2-methoxy-benzoic acid 4-[3-(3,4-Dichloro-benzenesulfonylamino)-benzoylamino]-2-methoxy-benzoic acid, MS (ISP): m/e=495.2 (M+H$^+$), was prepared in analogy to example 17, steps A to D. Step C was performed using 3,4-dichloro-benzenesulfonyl chloride and yielded 4-[3-(3,4-dichloro-benzenesulfonylamino)-benzoylamino]-2-methoxy-benzoic acid ethyl ester, which was hydrolyzed in step D.

Example 20

4-[3-(3-Chloro-benzenesulfonylamino)-benzoylamino]-2-methoxy-benzoic acid

4-[3-(3-Chloro-benzenesulfonylamino)-benzoylamino]-2-methoxy-benzoic acid, MS (ISP): m/e=459.3 (M+H$^+$), was prepared in analogy to example 17, steps A to D. Step C was performed using 3-chloro-benzenesulfonyl chloride and yielded 4-[3-(3-chloro-benzenesulfonylamino)-benzoylamino]-2-methoxy-benzoic acid ethyl ester, which was hydrolyzed in step D.

Example 21

4-[4-Chloro-3-(3-chloro-benzenesulfonylamino)-benzoylamino]-benzoic acid

4-[4-Chloro-3-(3-chloro-benzenesulfonylamino)-benzoylamino]-benzoic acid, MS (ISP): m/e=463.1 (M+H$^+$), was prepared in analogy to example 1, steps A to D. Step A was performed using 4-chloro-3-nitro-benzoyl chloride and yielded 4-(4-chloro-3-nitro-benzoylamino)-benzoic acid ethyl ester. This was reduced to 4-(4-Chloro-3-nitro-benzoylamino)-benzoic acid ethyl ester in step B. This was coupled with 3-chloro-benzenesulfonyl chloride in step C, yielding 4-[4-chloro-3-(3-chloro-benzenesulfonylamino)-benzoylamino]-benzoic acid ethyl ester, which was hydrolyzed in step D.

Example 22

4-[4-Chloro-3-(3,5-dichloro-benzenesulfonylamino)-benzoylamino]-benzoic acid 4-[4-Chloro-3-(3,5-dichloro-benzenesulfonylamino)-benzoylamino]-benzoic acid, MS (ISP): m/e=499.0 (M−H), was prepared in analogy to example 21, steps A to D. Step C was performed using 3,5-dichloro-benzenesulfonyl chloride and yielded 4-[4-chloro-3-(3,5-dichloro-benzenesulfonylamino)-benzoylamino]-benzoic acid ethyl ester, which was hydrolyzed in step D.

Example 23

4-[4-Chloro-3-(3-trifluoromethyl-benzenesulfonylamino)-benzoylamino]-benzoic acid 4-[4-Chloro-3-(3-trifluoromethyl-benzenesulfonylamino)-benzoylamino]-benzoic acid, MS (ISP): m/e=497.1 (M−H), was prepared in analogy to example 21, steps A to D. Step C was performed using 3-trifluoromethyl-benzenesulfonyl chloride and yielded 4-[4-chloro-3-(3-trifluoromethyl-benzenesulfonylamino)-benzoylamino]-benzoic acid ethyl ester, which was hydrolyzed in step D.

Example 24

4-[4-Chloro-3-(3-trifluoromethoxy-benzenesulfonylamino)-benzoylamino]-benzoic acid 4-[4-Chloro-3-(3-trifluoromethoxy-benzenesulfonylamino)-benzoylamino]-benzoic acid, MS (ISP): m/e=513.1 (M−H), was prepared in analogy to example 21, steps A to D. Step C was performed using 3-trifluoromethoxy-benzenesulfonyl chloride and yielded 4-[4-chloro-3-(3-trifluoromethoxy-benzenesulfonylamino)-benzoylamino]-benzoic acid ethyl ester, which was hydrolyzed in step D.

Example 25

4-[4-Chloro-3-(5-chloro-2-methoxy-benzenesulfonylamino)-benzoylamino]-benzoic acid 4-[4-Chloro-3-(5-chloro-2-methoxy-benzenesulfonylamino)-benzoylamino]-benzoic acid, MS (ISP): m/e=493.1 (M−H), was prepared in analogy to example 21, steps A to D. Step C was performed using 5-chloro-2-methoxy-benzenesulfonyl chloride and yielded 4-[4-chloro-3-(5-chloro-2-methoxy-benzenesulfonylamino)-benzoylamino]-benzoic acid ethyl ester, which was hydrolyzed in step D.

Example 26

4-[4-Chloro-3-(3,4-dichloro-benzenesulfonylamino)-benzoylamino]-benzoic acid 4-[4-Chloro-3-(3,4-dichloro-benzenesulfonylamino)-benzoylamino]-benzoic acid, MS (ISP): m/e=499.0 (M−H), was prepared in analogy to example 21, steps A to D. Step C was performed using 3,4-dichloro-benzenesulfonyl chloride and yielded 4-[4-chloro-3-(3,4-dichloro-benzenesulfonylamino)-benzoylamino]-benzoic acid ethyl ester, which was hydrolyzed in step D.

Example 27

4-[4-Chloro-3-(benzenesulfonylamino)-benzoylamino]-benzoic acid

4-[4-Chloro-3-(benzenesulfonylamino)-benzoylamino]-benzoic acid, MS (ISP): m/e=429.2 (M−H), was prepared in analogy to example 21, steps A to D. Step C was performed using benzenesulfonyl chloride and yielded 4-[4-chloro-3-(benzenesulfonylamino)-benzoylamino]-benzoic acid ethyl ester, which was hydrolyzed in step D.

Example 28

4-[4-Chloro-3-(2,5-dichloro-benzenesulfonylamino)-benzoylamino]-benzoic acid 4-[4-Chloro-3-(2,5-dichloro-benzenesulfonylamino)-benzoylamino]-benzoic acid, MS (ISP): m/e=497.0 (M−H), was prepared in analogy to example 21, steps A to D. Step C was performed using 2,5-dichloro-benzenesulfonyl chloride and yielded 4-[4-chloro-3-(2,5-dichloro-benzenesulfonylamino)-benzoylamino]-benzoic acid ethyl ester, which was hydrolyzed in step D.

Example 29

4-[4-Chloro-3-(3-fluoro-benzenesulfonylamino)-benzoylamino]-benzoic acid

4-[4-Chloro-3-(3-fluoro-benzenesulfonylamino)-benzoylamino]-benzoic acid, MS (ISP): m/e=447.1 (M−H), was prepared in analogy to example 21, steps A to D. Step C was performed using 3-fluoro-benzenesulfonyl chloride and yielded 4-[4-chloro-3-(3-fluoro-benzenesulfonylamino)-benzoylamino]-benzoic acid ethyl ester, which was hydrolyzed in step D.

Example 30

4-[4-Chloro-3-(2,5-dimethoxy-benzenesulfonylamino)-benzoylamino]-benzoic acid 4-[4-Chloro-3-(2,5-dimethoxy-benzenesulfonylamino)-benzoylamino]-benzoic acid, MS (ISP): m/e=489.2 (M−H), was prepared in analogy to example 21, steps A to D. Step C was performed using 2,5-dimethoxy-benzenesulfonyl chloride and yielded 4-[4-chloro-3-(2,5-dimethoxy-benzenesulfonylamino)-benzoylamino]-benzoic acid ethyl ester, which was hydrolyzed in step D.

Example 31

4-[3-(3-Chloro-benzenesulfonylamino)-4,5-dimethoxy-benzoylamino]-benzoic acid 4-[3-(3-Chloro-benzenesulfonylamino)-4,5-dimethoxy-benzoylamino]-benzoic acid, MS (ISP): m/e=489.2 (M+H$^+$), was prepared in analogy to example 1, steps A to D. Step A was performed using 3,4-dimethoxy-5-nitro-benzoyl chloride and yielded 4-(3,4-dimethoxy-5-nitro-benzoylamino)-benzoic acid ethyl ester. This was reduced to 4-(3,4-dimethoxy-5-nitro-benzoylamino)-benzoic acid ethyl ester in step B. This was coupled with 3-chloro-benzenesulfonyl chloride in step C, yielding 4-[3-(3-chloro-benzenesulfonylamino)-4,5-dimethoxy-benzoylamino]-benzoic acid ethyl ester, which was hydrolyzed in step D.

Example 32

4-[3-(3,5-Dichloro-benzenesulfonylamino)-4,5-dimethoxy-benzoylamino]-benzoic acid 4-[3-(3,5-Dichloro-benzenesulfonylamino)-4,5-dimethoxy-benzoylamino]-benzoic acid, MS (ISP): m/e=523.1 (M−H), was prepared in analogy to example 31, steps A to D. Step C was performed using 3,5-dichloro-benzenesulfonyl chloride and yielded 4-[3-(3,5-dichloro-benzenesulfonylamino)-4,5-dimethoxy-benzoylamino]-benzoic acid ethyl ester, which was hydrolyzed in step D.

Example 33

4-[3,4-Dimethoxy-5-(3-trifluoromethyl-benzenesulfonylamino)-benzoylamino]-benzoic acid 4-[3,4-Dimethoxy-5-(3-trifluoromethyl-benzenesulfonylamino)-benzoylamino]-benzoic acid, MS (ISP): m/e=523.1 (M−H), was prepared in analogy to example 31, steps A to D. Step C was performed using 3-trifluoromethyl-benzenesulfonyl chloride and yielded 4-[3,4-dimethoxy-5-(3-trifluoromethyl-benzenesulfonylamino)-benzoylamino]-benzoic acid ethyl ester, which was hydrolyzed in step D.

Example 34

4-[3-(5-Chloro-2-methoxy-benzenesulfonylamino)-4,5-dimethoxy-benzoylamino]-benzoic acid 4-[3-(5-Chloro-2-methoxy-benzenesulfonylamino)-4,5-dimethoxy-benzoylamino]-benzoic acid, MS (ISP): m/e=519.2 (M−H), was prepared in analogy to example 31, steps A to D. Step C was performed using 5-chloro-2-methoxy-benzenesulfonyl chloride and yielded 4-[3-(5-chloro-2-methoxy-benzenesulfonylamino)-4,5-dimethoxy-benzoylamino]-benzoic acid ethyl ester, which was hydrolyzed in step D

Example 35

4-[3-(3,4-Dichloro-benzenesulfonylamino)-4,5-dimethoxy-benzoylamino]-benzoic acid 4-[3-(3,4-Dichloro-benzenesulfonylamino)-4,5-dimethoxy-benzoylamino]-benzoic acid, MS (ISP): m/e=523.1 (M−H), was prepared in analogy to example 31, steps A to D. Step C was performed using 3,4-dichloro-benzenesulfonyl chloride and yielded 4-[3-(3,4-dichloro-benzenesulfonylamino)-4,5-dimethoxy-benzoylamino]-benzoic acid ethyl ester, which was hydrolyzed in step D.

Example 36

4-[3-(benzenesulfonylamino)-4,5-dimethoxy-benzoylamino]-benzoic acid

4-[3-(benzenesulfonylamino)-4,5-dimethoxy-benzoylamino]-benzoic acid, MS (ISP): m/e=455.2 (M−H), was prepared in analogy to example 31, steps A to D. Step C was performed using benzenesulfonyl chloride and yielded 4-[3-(benzenesulfonylamino)-4,5-dimethoxy-benzoylamino]-benzoic acid ethyl ester, which was hydrolyzed in step D.

Example 37

4-[3-(2,5-Dichloro-benzenesulfonylamino)-4,5-dimethoxy-benzoylamino]-benzoic acid 4-[3-(2,5-Dichloro-benzenesulfonylamino)-4,5-dimethoxy-benzoylamino]-benzoic acid, MS (ISP): m/e=523.1 (M−H), was prepared in analogy to example 31, steps A to D. Step C was performed using 2,5-dichloro-benzenesulfonyl chloride and yielded 4-[3-(2,5-dichloro-benzenesulfonylamino)-4,5-dimethoxy-benzoylamino]-benzoic acid ethyl ester, which was hydrolyzed in step D.

Example 38

4-[3-(3-Chloro-benzenesulfonylamino)-benzoylamino]-2-fluoro-benzoic acid

4-[3-(3-Chloro-benzenesulfonylamino)-benzoylamino]-2-fluoro-benzoic acid was Prepared as Illustrated in Scheme 2:

Step A)

A solution of 3-chloro-benzenesulfonyl chloride (2.68 g, 13.0 mmol) in toluene (10.0 ml) was warmed to 100° C. and treated with a solution of 3-amino-benzoic acid ethyl ester (2.00 g, 12.0 mmol) in toluene (10.0 ml). The mixture was stirred at 100° C. for 1 h, then cooled to 0° C. for 1 h. The precipitated solid was filtered, washing with toluene. Drying of the solid under high vacuum yielded 3-(3-chloro-benzenesulfonylamino)-benzoic acid ethyl ester (4.03 g, 98%) as an off-white solid, which was used crude in the following reaction.

Step B)

A solution of 3-(3-chloro-benzenesulfonylamino)-benzoic acid ethyl ester (4.03 g, 12.0 mmol) in ethanol (20.0 ml) was treated with 3N KOH (12.0 ml) and stirred at room temperature overnight. The mixture was then acidified with 3N HCl and the resulting slurry cooled to 0° C. The precipitated solid was filtered, washing with ethanol and dried under vacuum, yielding 3-(3-chloro-benzenesulfonylamino)-benzoic acid (2.61 g, 70%) as an off-white solid, MS (ISP): m/e=310.0 (M−H).

Step C)

A solution of 3-(3-chloro-benzenesulfonylamino)-benzoic acid (31.1 mg, 0.10 mmol) in DMF (0.5 ml) was added to 4-amino-2-fluoro-benzoic acid ethyl ester (20.1 mg, 0.11 mmol). Diisopropyl-ethyl-amine (0.035 ml) was added, followed by a solution of HATU (57.0 mg, 0.15 mmol) in DMF (0.5 ml). The mixture was shaken at room temperature overnight, then diluted with ethyl acetate (4.0 ml) and water (2.0 ml). The organic phase was separated and evaporated. The residue was dissolved in ethanol (0.60 ml) and treated with 3N KOH (0.40 ml). The mixture was shaken at room temperature overnight, then acidified to pH 2 with 3N HCl. Purification by preparative HPLC (ZORBAX Eclipse XDB-C18, 21.2×50 mm, 5 µm, gradient acetonitrile/water+0.1% formic acid) yielded the title compound (7.0 mg, 15%) as a white solid, MS (ISP): m/e=447.0 (M−H).

4-Amino-2-fluoro-benzoic acid ethyl ester was synthesized as illustrated in the following scheme:

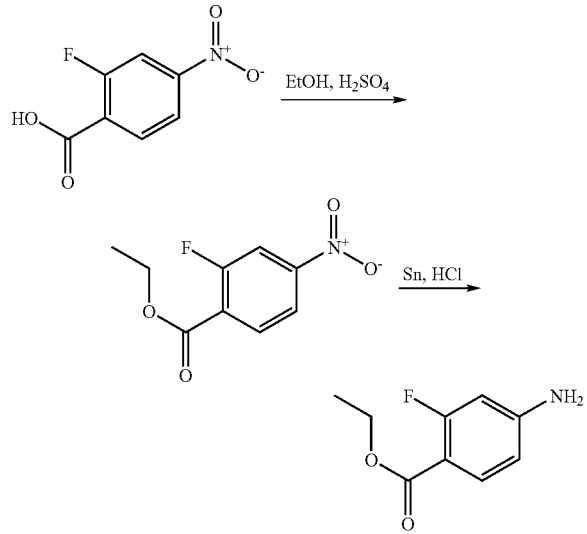

Step A)

A solution of 2-fluoro-4-nitro-benzoic acid (1.0 g, 5.0 mmol) in ethanol (10.0 ml) was treated with concentrated sulfuric acid (0.30 ml) and stirred at reflux overnight. On cooling to room temperature and then to 0° C. a crystalline precipitate formed. This was filtered washing with ethanol/water 2:1, and dried under vacuum, yielding 2-fluoro-4-nitro-benzoic acid ethyl ester (0.75 g, 65%) as an off-white crystalline solid.

Step B)

A solution of 2-fluoro-4-nitro-benzoic acid ethyl ester (0.72 g, 3.40 mmol) in THF (11.0 ml) was treated with tin metal (0.81 g, 6.80 mmol) and 6N HCl (5.43 ml). The mixture was warmed to 50° C. and stirred for 30 min. After cooling to room temperature, the solvent was evaporated. The residue was cooled to 0° C. and treated with 10% NaOH (20.0 ml). The resulting suspension was filtered and the solid washed with water. The solid was then redissolved in THF and filtered through a membrane to eliminate traces of metal. The filtrate was evaporated and the residue triturated in diisopropyl ether to afford after filtration 4-amino-2-fluoro-benzoic acid ethyl ester (0.55 g, 89%) as a light yellow solid, MS (ISP): m/e=184.1 (M+H⁺).

Example 39

5-[3-(3-Chloro-benzenesulfonylamino)-benzoylamino]-pyridine-2-carboxylic acid

5-[3-(3-Chloro-benzenesulfonylamino)-benzoylamino]-pyridine-2-carboxylic acid, MS (ISP): m/e=430.3 (M−H), was prepared in analogy to example 38, steps A to C. Step C was performed using 5-amino-pyridine-2-carboxylic acid ethyl ester.

5-Amino-pyridine-2-carboxylic acid ethyl ester was synthesized as illustrated in the following scheme:

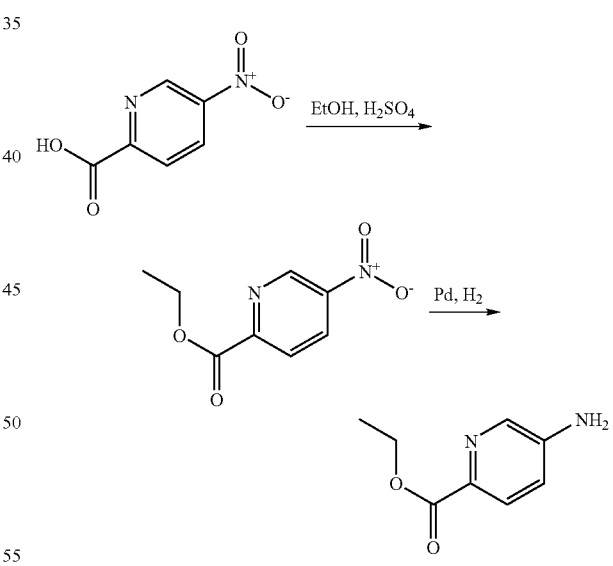

Step A)

A solution of 5-amino-pyridine-2-carboxylic acid (1.0 g, 5.9 mmol) in ethanol (15.0 ml) was treated with concentrated sulfuric acid (0.30 ml) and stirred at reflux overnight. The mixture was cooled to 0° C. and treated with 1M Na$_2$CO$_3$ until pH 8 was reached (4.0 ml). A precipitate formed, which was filtered washing with ethanol/water 2:1, and dried under vacuum, yielding 5-amino-pyridine-2-carboxylic acid ethyl ester (1.03 g, 89%) as a white solid, MS (EI): m/e=196.0 (M⁺).

Step B)

A solution of 5-amino-pyridine-2-carboxylic acid ethyl ester (1.0 g, 5.0 mmol) in ethanol (150.0 ml) was flushed with argon, then treated with palladium 10% on carbon (0.13 g). The flask was evacuated and flushed with hydrogen. The mixture was stirred at room temperature for 1 h, then filtered and the filtrate evaporated. 5-Amino-pyridine-2-carboxylic acid ethyl ester (0.76 g, 91%) was obtained as a white powder, MS (ISP): m/e=167.4 (M+H$^+$).

Example 40

3-(3-Chloro-benzenesulfonylamino)-[4-(tetrazol-5-yl)-phenyl]-benzamide 3-(3-Chloro-benzenesulfonylamino)-[4-tetrazol-5-yl)-phenyl]-benzamide was prepared as illustrated in scheme 3.

A microwave vial was charged with a solution of 3-(3-chloro-benzenesulfonylamino)-N-(4-cyano-phenyl)-benzamide (0.46 g, 1.12 mmol) in dimethylformamide (20.0 ml), ammonium chloride (1.11 g, 21 mmol, 18.5 equiv.) and sodium azide (1.31 g, 20 mmol, 18 equiv.) and irradiated in a microwave oven at 155° C. for 75 min. The mixture was diluted with saturated sodium hydrogenocarbonate and the phases were separated. The aqueous phase was washed with ethyl acetate and the organic phases were discarded. The aqueous phase was acidified with HCl (1N) and extracted with ethyl acetate. The combined organic phases were dried over sodium sulfate, filtered and the solvent removed in vacuo. The crude compound was triturated in dichloromethane and the white solid was filtered and dried under high vacuum. The title compound, MS (ISP): m/e=453.3 (M–H) was obtained as a white solid, 0.40 g (80%).

3-(3-Chloro-benzenesulfonylamino)-N-(4-cyano-phenyl)-benzamide was obtained in analogy to example 1, using 4-amino-benzonitrile instead of 4-amino benzoic acid ethyl ester in step 1.

Example 41

3-(5-Chloro-2-methoxy-benzenesulfonylamino)-[4-(tetrazol-5-yl)-phenyl]-benzamide 3-(5-Chloro-2-methoxy-benzenesulfonylamino)-[4-(tetrazol-5-yl)-phenyl]-benzamide, MS (ISP): m/e=483.0 (M–H), was obtained as described in example 40, using 3-(5-chloro-2-methoxy-benzenesulfonylamino)-N-(4-cyano-phenyl)-benzamide as starting material.

3-(5-Chloro-2-methoxy-benzenesulfonylamino)-N-(4-cyano-phenyl)-benzamide was obtained in analogy to example 1, using 4-amino-benzonitrile instead of 4-amino benzoic acid ethyl ester in step 1.

Example 42

3-(5-Chloro-2-methoxy-benzenesulfonylamino)-N-[4-(5-thioxo-4,5-dihydro-[1,2,4]oxadiazol-3-yl)-phenyl]-benzamide 3-(5-Chloro-2-methoxy-benzenesulfonylamino)-N-[4-(5-thioxo-4,5-dihydro-[1,2,4]oxadiazol-3-yl)-phenyl]-benzamide was obtained as illustrated in scheme 3.

Step A)

Hydroxylamine hydrochloride (0.24 mg, 3 mmol) was suspended in dimethyl sulfoxide under an argon atmosphere. Triethylamine (0.34 g, 3 mmol) was added dropwise. The mixture was stirred at room temperature for 15 min then filtered, washing with dry tetrahydrofuran. The filtrate was concentrated under vacuum. The resulting solution in dimethyl sulfoxide was treated with 3-(5-chloro-2-methoxy-benzenesulfonylamino)-N-(4-cyano-phenyl)-benzamide (0.30 g, 0.68 mmol) and the mixture was warmed to 75° C. and stirred for 2 hours. The mixture was cooled to room temperature then diluted with water and extracted with ethyl acetate. The organic phase was extracted with HCl 0.5 N. The heterogeneous aqueous solution was adjusted to pH 9-10 with NaOH 0.5N, then extracted with ethyl acetate. The combined organic phases were dried over sodium sulfate and evaporated to yield 3-(5-chloro-2-methoxy-benzenesulfonylamino)-N-[4-(N-hydroxycarbamimidoyl)-phenyl]-benzamide as a light green solid, MS (ISP): m/e=473.2 (M–H), which was used as such in the following reaction (0.23 g, 73%)

Step B)

3-(5-Chloro-2-methoxy-benzenesulfonylamino)-N-[4-(N-hydroxycarbamimidoyl)-phenyl]-benzamide (110 mg, 0.23 mmol) was diluted in acetonitrile (2 ml) under argon. 1,1'-Thiocarbonyldiimidazole (TCDI) (68 mg, 0.38 mmol, 1.65 equiv.) was then added, followed by 1,5-diazabicyclo[4.3.0]non-5-ene (DBN) (114 mg, 3.95 equiv.). The mixture was stirred at room temperature for 6 hours, then the solvents were evaporated. The residue was diluted with water and the pH was adjusted to 4 with HCl 1N. The aqueous phase was extracted with ethyl acetate, and the organic phase evaporated. The residue was dissolved in NaOH 1N, and washed with ether. The aqueous solution was adjusted to pH 4 with HCl 1N and then extracted with ethyl acetate. The organic phase was dried over sodium sulfate and evaporated. Purification via flash chromatography (dichloromethane/methanol) yielded the title compound as a light yellow solid (24 mg, 20%), MS (ISP): m/e=515.1 (M–H).

Example 43

3-(5-Chloro-2-methoxy-benzenesulfonylamino)-N-[4-(2-oxo-2,3-dihydro-[1,2,3,5]oxathiadiazol-4-yl)-phenyl]-benzamide A solution of 3-(5-chloro-2-methoxy-benzenesulfonylamino)-N-[4-(N-hydroxycarbamimidoyl)-phenyl]-benzamide (110 mg, 0.23 mmol) in tetrahydrofuran (7.0 ml) under argon was treated with pyridine (37 mg, 2 equiv.) and cooled to 0° C. A solution of thionyl chloride (28 mg, 1.01 equiv.) in dichloromethane (1.0 ml) was then added dropwise in 6 min. The mixture was stirred at 0° C. for 20 min and then at room temperature for 45 min. The solvent was evaporated and the residue diluted with water and extracted with ethyl acetate. The organic phase was dried over sodium sulfate and evaporated. Purification via preparative HPLC (Column: ZORBAX ECLIPSE XDB-C18, 21.2×50 mm, 5 um, PN 970050-902, SN USDN001082. Gradient: 0-1.2 min: 10% CH3 CN in (water+0.1% HCO2H), 1.2-4.7 min: increasing of CH3CN from 10% to 95%, 4.7-5.7 min: 95% of CH3CN, 5.7-59 min: decreasing of CH3CN from 95% to 10%. Program end at 6 min. Flow:30 ml/min) yielded the title compound as a light green solid (11 mg, 9%), MS (ISP): m/e=519.1 (M–H).

Example 44

3-(5-Chloro-2-methoxy-benzenesulfonylamino)-N-[4-(5-oxo-4,5-dihydro-[1,2,4]oxadiazol-3-yl)-phenyl]-benzamide A solution of 3-(5-chloro-2-methoxy-benzenesulfonylamino)-N-[4-(N-hydroxycarbamimidoyl)-phenyl]-benzamide (145 mg, 0.30 mmol) in dimethylformamide (2.0 ml) was treated with pyridine (26 mg, 1.08 equiv.) and cooled to 0° C. Chloroformic acid 2-ethylhexyl ester (59 mg, 0.30 mmol, 1 equiv.) in DMF (0.1 ml) was added dropwise. The mixture was stirred at 0° C. for 30 min, then diluted with water and extracted with ethyl acetate. The combined organic phases were dried over sodium sulfate and evaporated. The residue was suspended in xylene and the mixture was stirred at 100° C. for 1 h and then at 145° C. for 1 h. After cooling to room temperature, the precipitated solid was filtered, washing with xylene, and dried under high vacuum to yield the title compound (115 mg, 75%) as a white solid, MS (ISP): m/e=499.0 (M–H).

Example 45

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example 46

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 47

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example 48

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg |
| | (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 49

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavouring additives and filled into sachets.

It is to be understood that the invention is not limited to the particular embodiments of the invention described above, as variations of the particular embodiments may be made and still fall within the scope of the appended claims.

The invention claimed is:
1. A compound of formula (I):

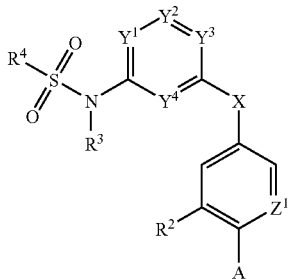

wherein
A is —C(O)OR$^1$ or selected from the group consisting of tetrazol-5-yl, 5-thioxo-4,5-dihydro-[1,2,4]oxadiazol-3-yl, 2-oxo-2,3-dihydro-[1,2,3,5]oxathiadiazol-4-yl and 5-oxo-4,5-dihydro-[1,2,4]oxadiazol-3-yl;
X is —C(O)N(R$^5$)—;
Y$^1$ is C(R$^6$);
Y$^2$ is C(R$^7$);
Y$^3$ is C(H);
Y$^4$ is C(R$^8$);
Z$^1$ is C(R$^9$);
R$^1$ is hydrogen or lower-alkyl;
R$^2$ is hydrogen, halogen, hydroxy, cyano, lower-alkyl, fluoro-lower-alkyl, lower-alkoxy, fluoro-lower-alkoxy; NH$_2$, N(H,lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ or lower-alkoxy;
R$^3$ is hydrogen;
R$^4$ is 3-chloro-phenyl, 3,4-dichloro-phenyl, 3,5-dichloro-phenyl or 5-chloro-2-methoxy—phenyl;
R$^5$ is hydrogen;
R$^6$, R$^7$ and R$^8$ independently from each other are selected from the group consisting of hydrogen, halogen, hydroxy, cyano, lower-alkyl, fluoro-lower-alkyl, lower-alkoxy, fluoro-lower-alkoxy; NH$_2$, N(H,lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ and lower-alkoxy;
R$^9$ is hydrogen, halogen, hydroxy, cyano, lower-alkyl, fluoro-lower-alkyl, lower-alkoxy, fluoro-lower-alkoxy; NH$_2$, N(H,lower-alkyl), N(lower-alkyl)$_2$, or lower-alkyl-C(O)—O—, wherein lower-alkyl is optionally substituted with hydroxy, halogen, NH$_2$, N(H,lower-alkyl), N(lower-alkyl)$_2$ or lower-alkoxy;
and pharmaceutically acceptable salts and esters thereof.
2. The compound according to claim 1, wherein A is —C(O)OR$^1$ and R$^1$ is as defined in claim 1.
3. The compound according to claim 1, wherein R$^1$ is hydrogen.
4. The compound according to claim 1, wherein R$^2$ is hydrogen, halogen or lower-alkoxy.
5. The compound according to claim 1, wherein R$^2$ is hydrogen.
6. The compound according to claim 1, wherein R$^6$ is hydrogen, halogen or lower-alkoxy.
7. The compound according to claim 1, wherein R$^6$ is hydrogen, chlorine or methoxy.
8. The compound according to claim 1, wherein R$^7$ is hydrogen or lower-alkoxy.
9. The compound according to claim 1, wherein R$^7$ is hydrogen or methoxy.
10. The compound according to claim 1, wherein R$^8$ is hydrogen.
11. The compound according to claim 1, wherein R$^9$ is hydrogen, halogen or lower-alkoxy.
12. The compound according to claim 1, wherein Z$^1$ is C(R$^9$) and R$^9$ is hydrogen.
13. A compound selected from the group consisting of
4-(3-Benzenesulfonylamino-benzoylamino)-benzoic acid,
4-[3-(4-Methoxy-benzenesulfonylamino)-benzoylamino]-benzoic acid,
4-[3-(3-Fluoro-benzenesulfonylamino)-benzoylamino]-benzoic acid,
4-[3-(3,4-Dichloro-benzenesulfonylamino)-benzoylamino]-benzoic acid,
4-[3-(2-Methoxy-benzenesulfonylamino)-benzoylamino]-benzoic acid,
4-[3-(3-Methoxy-benzenesulfonylamino)-benzoylamino]-benzoic acid,
4-[3-(2-Fluoro-benzenesulfonylamino)-benzoylamino]-benzoic acid,
4-[3-(3-Chloro-benzenesulfonylamino)-benzoylamino]-benzoic acid,
4-[3-(3-Trifluoromethyl-benzenesulfonylamino)-benzoylamino]-benzoic acid,
4-[3-(3,5-Dichloro-benzenesulfonylamino)-benzoylamino]-benzoic acid,
4-[3-(5-Chloro-2-methoxy-benzenesulfonylamino)-benzoylamino]-benzoic acid,
4-[3-(3-Difluoromethoxy-benzenesulfonylamino)-benzoylamino]-benzoic acid,
2-Methoxy-4-[3-(3-trifluoromethyl-benzenesulfonylamino)-benzoylamino]-benzoic acid,
4-[3-(3,5-Dichloro-benzenesulfonylamino)-benzoylamino]-2-methoxy-benzoic acid,
4-[3-(3,4-Dichloro-benzenesulfonylamino)-benzoylamino]-2-methoxy-benzoic acid,
4-[3-(3-Chloro-benzenesulfonylamino)-benzoylamino]-2-methoxy-benzoic acid,
4-[4-Chloro-3-(3-chloro-benzenesulfonylamino)-benzoylamino]-benzoic acid,
4-[4-Chloro-3-(3,5-dichloro-benzenesulfonylamino)-benzoylamino]-benzoic acid,
4-[4-Chloro-3-(3-trifluoromethyl-benzenesulfonylamino)-benzoylamino]-benzoic acid,
4-[4-Chloro-3-(3-trifluoromethoxy-benzenesulfonylamino)-benzoylamino]-benzoic acid,
4-[4-Chloro-3-(5-chloro-2-methoxy-benzenesulfonylamino)-benzoylamino]-benzoic acid,
4-[4-Chloro-3-(3,4-dichloro-benzenesulfonylamino)-benzoylamino]-benzoic acid,
4-[4-Chloro-3-(benzenesulfonylamino)-benzoylamino]-benzoic acid,
4-[4-Chloro-3-(2,5-dichloro-benzenesulfonylamino)-benzoylamino]-benzoic acid,
4-[4-Chloro-3-(3-fluoro-benzenesulfonylamino)-benzoylamino]-benzoic acid,
4-[4-Chloro-3-(2,5-dimethoxy-benzenesulfonylamino)-benzoylamino]-benzoic acid,
4-[3-(3-Chloro-benzenesulfonylamino)-4,5-dimethoxy-benzoylamino]-benzoic acid,
4-[3-(3,5-Dichloro-benzenesulfonylamino)-4,5-dimethoxy-benzoylamino]-benzoic acid, 4-[3,4-Dimethoxy-5-(3-trifluoromethyl-benzenesulfonylamino)-benzoylamino]-benzoic acid,
4-[3-(5-Chloro-2-methoxy-benzenesulfonylamino)-4,5-dimethoxy-benzoylamino]-benzoic acid,
4-[3-(3,4-Dichloro-benzenesulfonylamino)-4,5-dimethoxy-benzoylamino]-benzoic acid,
4-[3-(benzenesulfonylamino)-4,5-dimethoxy-benzoylamino]-benzoic acid,
4-[3-(2,5-Dichloro-benzenesulfonylamino)-4,5-dimethoxy-benzoylamino]-benzoic acid,
4-[3-(3-Chloro-benzenesulfonylamino)-benzoylamino]-2-fluoro-benzoic acid, and
and pharmaceutically acceptable salts and esters thereof.

14. The compound according to claim 13, selected from the group consisting of

4-[3-(3,4-Dichloro-benzenesulfonylamino)-benzoylamino]-benzoic acid,
4-[3-(3-Chloro-benzenesulfonylamino)-benzoylamino]-benzoic acid,
4-[3-(3,5-Dichloro-benzenesulfonylamino)-benzoylamino]-benzoic acid,
4-[3-(5-Chloro-2-methoxy-benzenesulfonylamino)-benzoylamino]-benzoic acid,
4-[4-Chloro-3-(3-chloro-benzenesulfonylamino)-benzoylamino]-benzoic acid,
4-[4-Chloro-3-(3,5-dichloro-benzenesulfonylamino)-benzoylamino]-benzoic acid,
4-[4-Chloro-3-(5-chloro-2-methoxy-benzenesulfonylamino)-benzoylamino]-benzoic acid,
4-[3-(3,5-Dichloro-benzenesulfonylamino)-4,5-dimethoxy-benzoylamino]-benzoic acid, and
4-[3-(5-Chloro-2-methoxy-benzenesulfonylamino)-4,5-dimethoxy-benzoylamino]-benzoic acid,
and pharmaceutically acceptable salts and esters thereof.

15. A pharmaceutical composition, comprising a therapeutically effective amount of a compound according to claim 1, and a pharmaceutically acceptable carrier and/or adjuvant.

* * * * *